(12) United States Patent
Andrieux

(10) Patent No.: US 10,813,441 B2
(45) Date of Patent: Oct. 27, 2020

(54) BELT FOR TRANSPORTING A MEDICAL DEVICE AND MAINTAINING SAME IN PLACE, AND CORRESPONDING KIT

(71) Applicant: OXSITIS, Chateaugay (FR)

(72) Inventor: Fabien Andrieux, Riom (FR)

(73) Assignee: OXSITIS, Chateaugay (FR)

( * ) Notice: Subject to any disclaimer, the term of this patent is extended or adjusted under 35 U.S.C. 154(b) by 154 days.

(21) Appl. No.: 15/780,103

(22) PCT Filed: Dec. 10, 2016

(86) PCT No.: PCT/FR2016/053323
§ 371 (c)(1),
(2) Date: May 30, 2018

(87) PCT Pub. No.: WO2017/103400
PCT Pub. Date: Jun. 22, 2017

(65) Prior Publication Data
US 2018/0360199 A1    Dec. 20, 2018

(30) Foreign Application Priority Data

Dec. 16, 2015    (FR) ...................... 15 62552

(51) Int. Cl.
*A45F 5/02*    (2006.01)
*A61F 5/02*    (2006.01)
*A61M 5/178*    (2006.01)

(52) U.S. Cl.
CPC .............. *A45F 5/021* (2013.01); *A61F 5/028* (2013.01); *A61M 5/178* (2013.01); *A61M 2209/088* (2013.01)

(58) Field of Classification Search
CPC ...... A45F 5/021; A61F 5/028; A61F 5/14244; A61M 5/178; A61M 2209/088; A61M 2005/1586; A61M 25/02
USPC ......................................................... 224/682
See application file for complete search history.

(56) References Cited

U.S. PATENT DOCUMENTS

| | | | | |
|---|---|---|---|---|
| 5,064,108 A | * | 11/1991 | Headley | A45F 3/14 224/259 |
| 5,259,831 A | * | 11/1993 | LeBron | A61F 5/022 602/19 |
| 5,665,057 A | | 9/1997 | Murphy | |
| 2005/0222654 A1 | * | 10/2005 | Brown | A61F 7/02 607/109 |
| 2009/0054844 A1 | | 2/2009 | Alyea et al. | |
| 2009/0089913 A1 | | 4/2009 | Ehrlickman | |

(Continued)

FOREIGN PATENT DOCUMENTS

EP    0075753 A1    4/1983

OTHER PUBLICATIONS

Written Opinion for related international application No. PCT/FR2016/053323, dated Mar. 29, 2017.

*Primary Examiner* — Corey N Skurdal

(57) ABSTRACT

The invention relates to a belt (C) for transporting a medical device and maintaining same in place, said belt comprising at least one member (21) for receiving the device. The belt (C) comprises at least two bands of textile material (1; 12) connected by four removable, adjustable-length straps (8 to 11). The band of flexible material (1; 12) is a quadrilateral with a length to width ratio of at least 1.5. The invention also relates to a corresponding kit.

14 Claims, 2 Drawing Sheets

(56) References Cited

U.S. PATENT DOCUMENTS

2009/0095783 A1\* 4/2009 Price .................. A45F 3/00
                                                 224/576
2013/0261523 A1  10/2013 Johnson
2019/0134362 A1\* 5/2019 Fee ................. A61M 25/02

\* cited by examiner

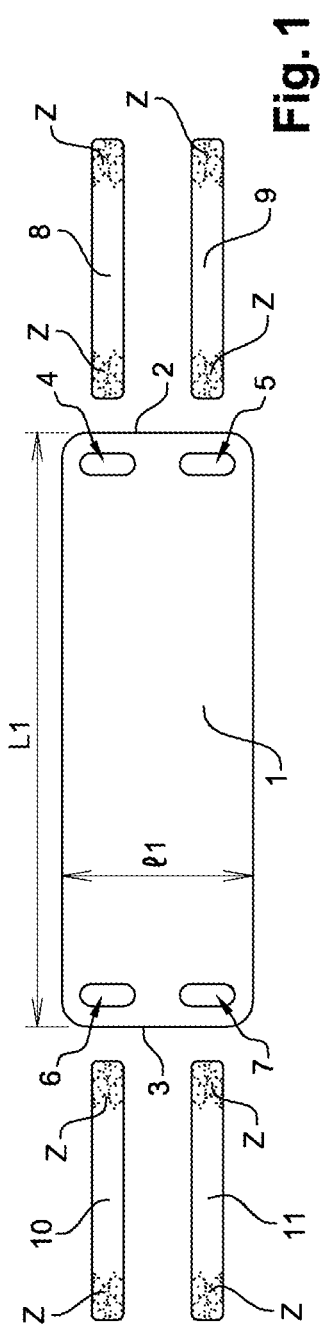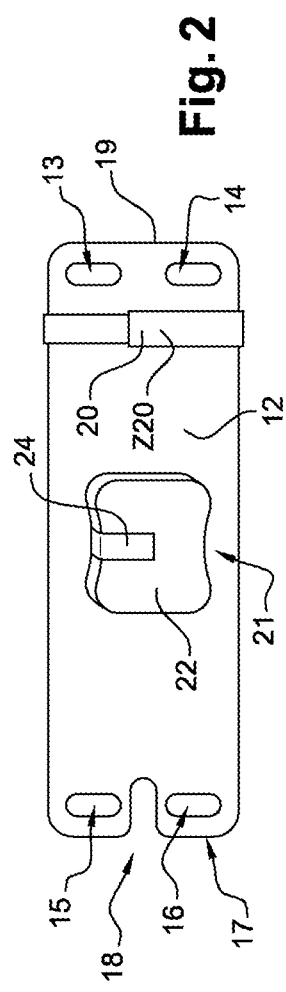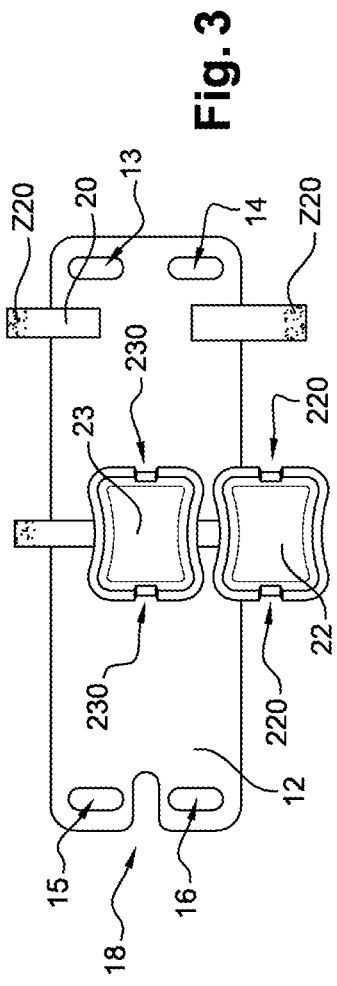

BELT FOR TRANSPORTING A MEDICAL DEVICE AND MAINTAINING SAME IN PLACE, AND CORRESPONDING KIT

BACKGROUND OF THE INVENTION

The present invention relates to a belt for transporting a medical device and maintaining same in place, as well as a corresponding kit.

For several pathologies, it is necessary for the patient to have constant treatment, day and night, without interruption. In such cases, the patient either must continuously take a drug or must continuously wear a medical device, irrespective of whether the device comprises a part implanted in the patient's body.

When the patient is hospitalized, or at least confined to bed, it is relatively easy to carry out such treatment, due to the absence or relative lack of movement by the patient. However, when the patient's general condition is satisfactory and the latter is able to have a social and/or professional life that is as close as possible to normal, the question of the mobility of the means for dispensing the drug and/or the medical device arises.

In particular, the patient is often required to move around with a receptacle for storing and/or dispensing a drug and/or a medical device and/or a power source for a medical device. In order to maintain the device or receptacle in place on the patient while limiting the bother caused by this transport as much as possible, various solutions are known. These in particular include those disclosed by WO-A-2009 045 532, which relates to a belt on which a pouch is fastened. Also known from EP-A-1,514,571 is a belt formed by a self-adhesive band that maintains an injection device in position for treatment also including a reservoir mounted on a moving carriage, or by WO-A-9,715,252, a belt for transporting a colostomy bag. Also known from EP-A-75,753 is a harness including two dorsal and ventral parts adjustable around the abdomen, this harness being kept on the patient's shoulders by two shoulder straps.

These various solutions are not fully satisfactory. Indeed, the weight and/or bulk of the medical device to be transported frequently generates, if not fatigue, at least bother for the patient wearing such belts.

The invention more particularly aims to resolve these drawbacks by proposing a belt for transporting a medical device and maintaining it in place that is easy to wear, without fatigue by the patient, while not hindering the latter's movements.

BRIEF SUMMARY OF THE INVENTION

To that end, the invention relates to a belt for transporting, and maintaining in place, a medical device including at least one member for receiving said device, said belt comprising at least one band of flexible material and at least one strap with an adjustable length, the band of flexible material being a quadrilateral, the length-to-width ratio of which is at least equal to 1.5, characterized in that it comprises two bands of textile material connected by four removable straps.

Thus, with such a width of the belt, comfortable maintenance of the latter is provided around a patient's waist. The weight of the device is distributed over a surface such that the traction exerted on the abdominal and lumbar regions of the patient is minimal. Furthermore, such a length-to-width ratio limits the displacement movements of the belt around the patient's waist. The presence of at least one band maintained adjustably by at least one strap makes it possible to adjust, optimally and in an individualized manner, the tension of the belt around the patient's waist. In other words, comfort is increased, while providing optimal maintenance of the device.

According to advantageous, but optional aspects of the invention, such a belt may comprise one or several of the following features:

The straps are provided at their free ends with self-adhesive zones.

A notch arranged on one end of a band and a maintaining member arranged near the other edge of the band form means for maintaining a cable, conduit or sheath.

The receiving member of the medical device is made from a rigid material.

The receiving member is formed from two parts with complementary shapes, one part forming a removable cover.

Passages for conduits, cables or sheaths are formed in the edges of the parts.

At least one of the bands is equipped with at least one other receiving member.

At least one other receiving member equipping at least one of the bands is a flexible pouch.

The belt comprises at least one band made from an impermeable flexible material.

The band of impermeable flexible material is equipped with a pouch for receiving a medical device, the pouch being provided with a sealing means.

The band of impermeable flexible material is equipped with a pouch for receiving a band of flexible material.

The invention also relates to a kit for transporting a medical device and maintaining same in place comprising at least one belt according to one of the preceding features, characterized in that it comprises at least two members for receiving two different medical devices, at least two bands of flexible material and at least four straps.

According to advantageous, but optional aspects of the invention, such a kit may comprise one or more of the following features:

it comprises at least two bands of flexible material with different dimensions and/or natures and at least four straps.

It comprises at least one band of impermeable flexible material.

BRIEF DESCRIPTION OF THE SEVERAL VIEWS OF THE DRAWINGS

The invention will be better understood, and other advantages thereof will appear more clearly upon reading the following description of several embodiments of the invention, provided non-limitingly and done in reference to the following drawings, in which:

FIG. 1 is a top view of one face of a first textile band and connecting straps, making up one embodiment of the invention, in a preassembly position, FIG. 2 is a top view, on the same scale, of one face of a second textile band making up the embodiment of FIG. 1, FIG. 3 is a view similar to FIG. 2, on the same scale, the receiving member of the medical device being in the open position.

DETAILED DESCRIPTION OF THE INVENTION

Figure 4:
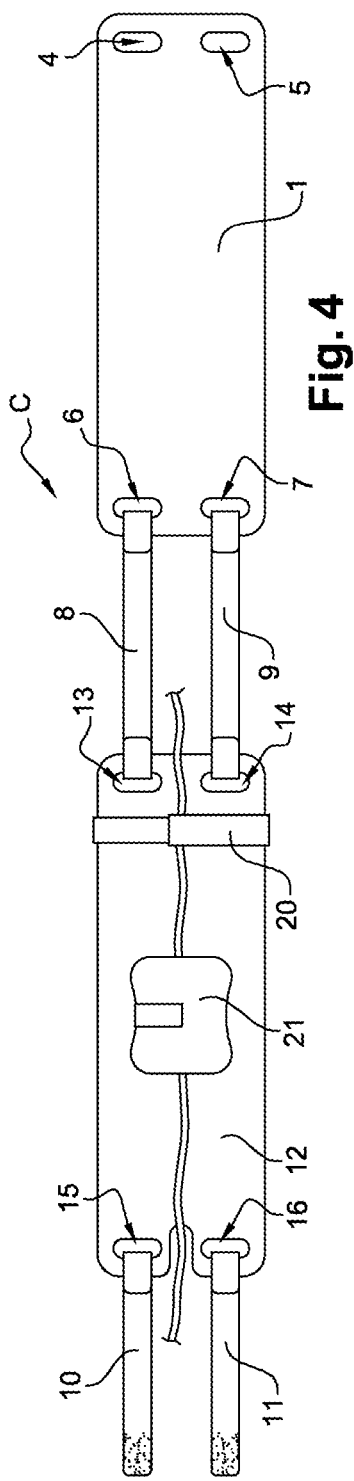
FIG. 4 is a top view, on the same scale, of a transport means, in the mounted configuration, made from bands illustrated in the preceding figures.

FIG. 1 illustrates a first band of flexible material 1. Here, the band 1 is made from a textile, in the case at hand polyester. Alternatively, it is made from polyamide, polyurethane or another synthetic or natural textile. The band 1 is, in all cases, made from a material that is not only flexible, but washable, nonallergenic, nonflammable and suitable for being worn by a person either on the clothing or directly in contact with the skin. The band 1 is a quadrilateral, therefore rectangular or square. Advantageously, it is rectangular.

The band 1 has a length L1 comprised between 4.5 cm and 40 cm for a width l1 comprised between 3 cm and 20 cm. Thus, one has a ratio L1/l1 at least equal to 1.5 and advantageously comprised between 1.5 and 2. In all cases, the band 1 must have a minimal width l1 of 3 cm. Such a minimal width l1 allows maintenance in position of the textile band 1, without the latter risking injuring the wearer of the belt and while limiting, if not avoiding, any risk of movement of the belt, by rotation around the waist.

The corners of the band 1 are rounded. The edges 2, 3 of the band 1 defining the width l1 are each provided with two through orifices 4 to 7. Here, the orifices 4 to 7 are elongated. In an alternative that is not illustrated, they have another shape and/or another dimension. Likewise, one can see that the number of orifices may be different, for example it is possible to provide three orifices on each edge, if the width of the band allows it. In all cases, the orifices 4 to 7 are suitable for providing the passage, with minimal play, of at least one flat strap 8 to 11. Here, four straps 8 to 11 are advantageously provided.

Each strap 8 to 11 is provided, at its free ends, with a means for fastening the strap to one end of another strap 11 to 8 or to the other free end of the same strap. In the case at hand, the fastening means is a self-adhesive zone Z arranged at the ends of the straps 8 to 11. One can easily see that other fastening means can be used, for example snaps, slide fasteners, magnets or the like, as long as these means are maneuverable quickly by the wearer of the belt.

FIG. 2 illustrates a second band of flexible material 12. Here, the nature of the flexible material is also a textile. The shape and the dimensions of the band 12 are similar to those of the band 1. Alternatively, they are different. In other words, the band 12 is rectangular. Like the first band 1, the band 12 is provided with four through orifices 13 to 16. These orifices 13 to 16 are similar to the orifices 4 to 7. Alternatively, they have different shapes and/or dimensions. The orifices 13 to 16 are arranged on the edges 17 to 19 of the band 12. They also allow the passage of the straps 8 to 11.

One edge 17, here on the left in FIG. 2, defining the width of the band 12, is provided, substantially in the median position, with a notch 18. This notch 18 serves to facilitate the passage of conduits and/or cables when the latter must pass between the belt and the patient's skin, for example when they are connected to an implantable medical device. Alternatively, the arrangement and/or the number of notches 18 are different, with the understanding that notches 18 can be provided on both edges 17, 19. In order to preserve the integrity of the cables and conduits, the edges of the notch 18 are rounded and advantageously equipped with padding.

The edge 19, opposite and parallel to the edge 17, is equipped with a member 20 for maintaining a conduit or a cable, not illustrated. The member 20 is located near the orifices 13, 14. Here, the member 20 is formed by a strap provided with self-adhesive free ends Z20, thus making it possible to form a loop. Alternatively, the loop closure of the strap 20 is obtained by other means known in themselves, for example by snaps, magnets or a slide closure.

Substantially in the median position, the band 12 is equipped with a member 21 for receiving a medical device or at least part of the latter. A medical device for example refers to a control unit and/or a unit for recording physiological data, a syringe, a battery, a pump, a container, a means for storing and/or dispensing a drug or another member making up a medical device or even a complete medical device, with the understanding that part of such a device is generally, but not necessarily, implanted in the patient's body, for example through a venous route. In all cases, the use of the device requires the maintenance, on the patient's body, of at least part of the device, if not permanently, at least for several consecutive hours.

The receiving member 21 is made from a rigid material, suitable for contact with a medical device, therefore at least neutral with respect to the latter, in particular from an electromagnetic perspective. Advantageously, the member 21 is easy to clean and disinfect. The member 21 is also suitable for being worn by a patient. The member 21 assumes the form of a rigid unit in two parts 22, 23. One part 22 forms a cover with a shape complementary to the other part 23, called receiving part.

This part 23 has a shape complementary to that of the device, so as to receive the device with minimal play, avoiding any movement of the device when it is in place in the part 23. In an alternative that is not illustrated, wedging members such as foam blocks are provided.

When the cover 22 is in position on the receiving part 23, as illustrated in FIGS. 2 and 4, the volume defined by the parts 22, 23, therefore de facto the working inner volume of the member 21, is closed. Thus, the medical device is protected from dust and/or sprayed water while allowing, if needed, the dissipation of the heat generated by the operation of the device and/or the wireless communication of the device with a control member or the collection of remote data from the member 21.

One can see that, alternatively, a sealing gasket is provided between the parts 22 and 23 in order to improve the protection against sprayed water. Such a gasket can be replaced by a geometric configuration of the cover 22 that partially covers the part 23, thus limiting any entry of water into the volume of the member 21. In another embodiment that is not illustrated, a removable dust cover makes it possible to cover the member 21 and protect the medical device against any entry of water.

Notches 220, 230, advantageously at the edges covered by a flexible material, for example an elastomer, are arranged in at least one of the parts 22, 23 in order to allow the passage of cables, sheets and/or conduits connecting the device to the patient's body. Here, each part 22, 23 is provided with two identical notches 220, 230, across from one another on opposite edges of the parts 22, 23. According to the illustrated advantageous embodiment, the passage notches 220, 230 for the cables, sheets and conduits are formed by concave zones arranged in the parts 22, 23. These zones are not adjacent when the parts 22, 23 are in the closed configuration, as shown in FIGS. 2 and 4.

The parts 22, 23 are maintained in the closed configuration by a closing member 24. This member 24 is easy to manipulate, is not sensitive to water and is lightweight. Advantageously, it is formed by a self-adhesive band.

As illustrated in FIG. 3, when one wishes to place a medical device, not illustrated for greater legibility, in the member 21, aside from configuring the parts 22, 23 in the open position, the band 20 should be released in order to pass the cables, sheets and/or conduits on the textile band 12. This can be done before placing the belt around the patient's waist or, alternatively, once the belt has been placed around the patient's waist. In all cases, it is advantageous to place the medical device in the member 21 when the bands 1, 12 are connected to one another by the straps 8 to 11 to form the belt C.

As shown by FIG. 3, to produce the belt C, the bands of flexible material are united, in the example two textile bands 1, 12, by the straps, here four straps 8 to 11, inserted into the orifices 4 to 7. The belt C should be allowed to go around the patient's waist without gripping, while allowing the movements of the patient and keeping the belt C in place, i.e., without the latter performing rotating movements or vertical displacements around the patient's waist when the latter moves. To that end, it is easy to adjust, precisely and as many times as necessary, the length of the straps 4 to 7 once the belt C is in place, for example depending on the clothing worn by the patient.

The width of each textile band 1, 12 making up the belt C allows a regular distribution of the pressure exerted by the tension of the belt and the weight of the device on a sufficient surface for daily and continuous wear of the belt C not to be restrictive. Furthermore, such a configuration, in at least one and preferably two bands of flexible material that are relatively wide relative to their lengths, makes it possible, advantageously combined with the nature of the flexible material, here textile, to avoid or at least limit any heating phenomenon. The presence of open mesh zones in the bands also contributes to limiting the appearance of heating or allergic reactions, while facilitating, inter alia, the evacuation of sweat when the belt C is worn directly on the skin. Such a belt C makes it possible to maintain a device able to weigh up to 1000 g, knowing that the weight of the belt is comprised between 70 grams and 300 grams.

In another embodiment that is not shown, the member 21 is fastened removably, for example by a self-adhesive band, on the textile band 12. Alternatively, the fastening is done by another means known in itself, such as snaps, a slide closure, a magnetic link or the like.

Figure 5:
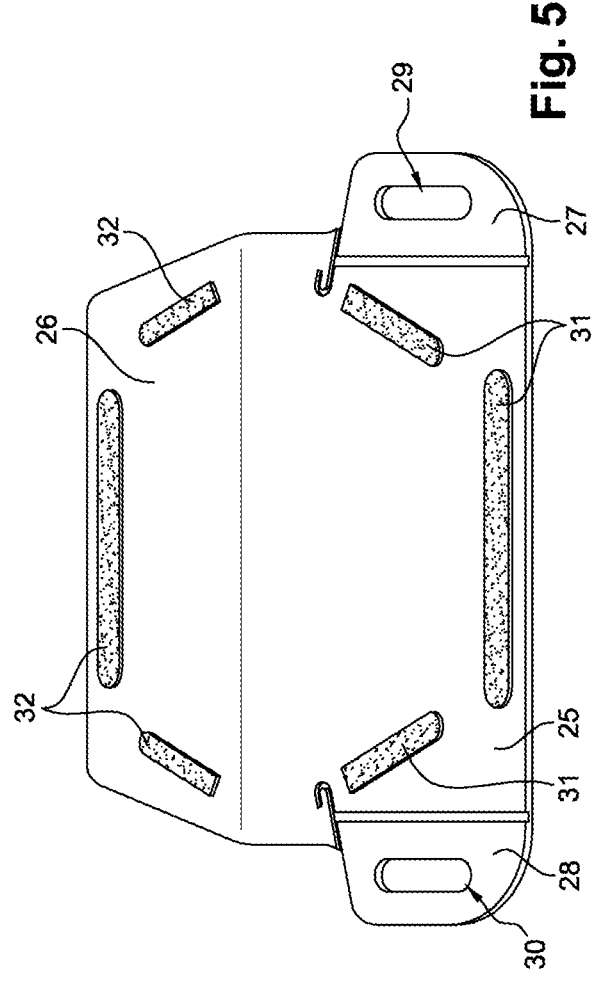
FIG. 5 is a top view of a band made from impermeable flexible material according to another embodiment of the invention.

FIG. 5 illustrates another embodiment of the invention in which a band 25 made from an impermeable flexible material is illustrated. Here, the band 25 is made from polyurethane of the transparent and biocompatible TPU type. Alternatively, it is made from PVC or another biocompatible and impermeable polymer. The band 25 comprises a central volume that is removably sealable by a flap 26.

In other words, the band 25 includes a pouch for receiving either a device or, like in the illustrated example, a band 1 or 12. The edges 27, 28 of the band 25 are provided with passage orifices 29, 30, respectively, for straps 8 to 11. Self-adhesive bands 31 fastened on the band 25 provide the maintenance in the closed position of the flap 26 by cooperation with complementary self-adhesive bands 32 fastened on the flap 26.

One can see that, alternatively, such a band made from impermeable material is configured in a sleeve, for example open at the ends, able to receive the band 1 equipped with the device 21. Alternatively, the inner volume of the band 25 is suitable for receiving the device 21. In all cases, such a band 25 allows the patient to transport the medical device when he must visit a wet environment, for example when going out in the rain or taking a shower.

It is thus possible to propose a kit having at least one band of flexible material 1; 12, at least one strap 8 to 11 and at least two members 21 for receiving two different medical devices. The members 21 that make up the kit have shapes and/or dimensions suitable for the devices to be maintained. Such a kit may advantageously include bands of flexible material with different numbers and/or dimensions and/or natures of materials, in particular widths, from those described. In particular, according to one preferred embodiment, the kit comprises two bands of flexible material, at least two and advantageously four straps, and a band made from an impermeable flexible material. In other words, such a kit makes it possible to produce, in a customized and nonpermanent manner, a belt C that is particularly easy to adapt to the device to be received and/or to the patient needing to wear the belt C.

Alternatively, the component straps 8 to 11 are made from a resilient material. Likewise, the straps 1; 12 can be manufactured, at least in part, with a resilient material. The use of resilient material participates in facilitating the adjustment of the belt C by increasing the adjustment range of the length thereof.

Alternatively, the receiving member 21 is provided with means for signaling the presence and/or operation of a medical device when the latter is housed in the member. Examples include a visual color marking on a visible face of the member in the closed configuration, an LED and/or the emission of a sound signal in the closed or open configuration or any other signaling means.

Likewise, it is alternatively possible to provide so-called mistake-proofing means allowing the user only to introduce a specific medical device or only to introduce a device into the receiving member in a specific orientation.

In another embodiment, it is provided to maintain more than one device or more than one component member of a device on such a belt. In this case, the band 12 is adapted.

In another embodiment, the belt C is equipped with other receiving members, for example flexible pouches to contain a document, keys or a canister.

In another embodiment, at least one band is equipped with flexible solar panels, known in themselves, allowing at least partial recharging of a motor member of the medical device.

One can easily see that the invention is also applicable in the veterinary field, as long as the dimensions and/or shape of the bands and straps are adapted.

The invention claimed is:

1. A belt for transporting a medical device, the belt comprising:
    two bands of flexible material, each having parallel upper and lower sides that are perpendicular to a left side and a right side and a length to width ratio of which at least equal to 1.5;
    four straps, each with an adjustable length and two opposing free ends, wherein each of the four straps are removably secured to the two bands, and wherein each of the two opposing free ends of each of the four straps is removably secured to a different band of the two bands;
    wherein each band of the two bands is secured to another band of the two bands by two straps of the four straps secured along the left side and two other straps of the four straps secured along the ride side; and
    at least one receiving member for receiving the medical device secured to one band of the two bands.

2. The belt according to claim 1, wherein each of the four straps is provided with self-adhesive zones at each of the two opposing free ends.

3. The belt according to claim 1, wherein a notch arranged on one edge of the one band of the two bands and a maintaining member arranged near another edge of the one band of the two bands form a means for maintaining a cable, conduit, or sheath.

4. The belt according to claim 1, wherein the at least one receiving member is made from a rigid material.

5. The belt according to claim 4, wherein the at least one receiving member is formed from two parts with complementary shapes, one part of the two parts forming a removable cover.

6. The belt according to claim 5, wherein passages for conduits, cables, or sheaths are formed in edges of the two parts.

7. The belt according to claim 1, further comprising at least two receiving members secured to the one band of the two bands.

8. The belt according to claim 7, wherein at least one of the at least two receiving members is a flexible pouch.

9. The belt according to claim 1, further comprising at least one band (25) made from an impermeable flexible material.

10. The belt according to claim 9, wherein the at least one band (25) of impermeable flexible material is equipped with a pouch for receiving a medical device, the pouch being provided with a sealing means.

11. The belt according to claim 9, wherein the at least one band (25) of impermeable flexible material is equipped with a pouch for receiving a single band of flexible material.

12. A kit for transporting a medical device and maintaining same in place comprising:
   at least one belt according to claim 1, at least two members for receiving two different medical devices, at least two bands of flexible material, and at least four straps.

13. The kit according to claim 12, wherein the at least two bands of flexible material different dimensions or natures.

14. The kit according to claim 12, further comprising at least one band (25) of impermeable flexible material.

* * * * *